US00RE46494E

(19) United States
(12) Reissued Patent
Bauer et al.

(10) Patent Number: US RE46,494 E
(45) Date of Reissued Patent: Aug. 1, 2017

(54) LOAD-CARRYING BODY FOR REDUCING TORSIONAL AND TENSILE LOADING ON ELECTRONIC COMPONENTS IN AN IMPLANTABLE MEDICAL ELECTRICAL LEAD

(71) Applicant: Greatbatch Ltd., Clarence, NY (US)

(72) Inventors: Ryan T. Bauer, Plymouth, MN (US); Warren S. Dabney, Lake Oswego, OR (US); Robert A. Stevenson, Canyon Country, CA (US)

(73) Assignee: Greatbatch Ltd., Clarence, NY (US)

(21) Appl. No.: 14/447,747

(22) Filed: Jul. 31, 2014

Related U.S. Patent Documents

Reissue of:
(64) Patent No.: 8,244,373
Issued: Aug. 14, 2012
Appl. No.: 12/914,048
Filed: Oct. 28, 2010

U.S. Applications:
(63) Continuation-in-part of application No. 12/891,292, filed on Sep. 27, 2010, now Pat. No. 8,437,865, which is a continuation-in-part of application No. 12/873,862, filed on Sep. 1, 2010, now Pat. No. 8,224,440, and a continuation-in-part of application No. 12/607,234, filed on Oct. 28, 2009, now Pat. No. 8,175,700, which is a continuation-in-part of application No. 11/558,349, filed on Nov. 9, 2006, now Pat. No. 7,945,322, said application No. 12/873,862 is a continuation-in-part of application No. 11/943,854, filed on Nov. 21, 2007, now Pat. No. 7,853,325.

(60) Provisional application No. 61/256,658, filed on Oct. 30, 2009, provisional application No. 61/303,109, filed on Feb. 10, 2010, provisional application No. 61/243,643, filed on Sep. 18, 2009, provisional application No. 61/314,676, (Continued)

(51) Int. Cl.
*A61N 1/00* (2006.01)
*A61N 1/04* (2006.01)
*A61N 1/06* (2006.01)

(52) U.S. Cl.
CPC *A61N 1/04* (2013.01); *A61N 1/06* (2013.01)

(58) Field of Classification Search
None
See application file for complete search history.

(56) References Cited

U.S. PATENT DOCUMENTS 5,851,227 A * 12/1998 Spehr ..... A61N 1/057 607/116
6,813,521 B2 * 11/2004 Bischoff ..... A61N 1/0573 600/375

(Continued)

*Primary Examiner* — Glenn K Dawson
(74) *Attorney, Agent, or Firm* — Michael F. Scalise

(57) ABSTRACT

A load-carrying body for reducing torsional and tensile loading on electrical components in an implantable medical electrical lead includes an electronic component disposed in-line with the implantable medical electrical lead, and a casing for the electronic component. The electronic component has a proximal end conductively coupled to a lead conductor and a distal end conductively coupled to a lead electrode. The casing is mechanically coupled to the lead so as to isolate the electrical component from torque or tensile loads applied to the lead, the lead electrode, or both.

23 Claims, 10 Drawing Sheets

Related U.S. Application Data filed on Mar. 17, 2010, provisional application No. 61/245,720, filed on Sep. 25, 2009.

(56) References Cited

U.S. PATENT DOCUMENTS

| | | | | |
|---|---|---|---|---|
| 6,944,489 | B2 * | 9/2005 | Zeijlemaker et al. | 600/373 |
| 7,092,764 | B2 * | 8/2006 | Williams | A61N 1/056 607/115 |
| 7,853,325 | B2 * | 12/2010 | Dabney | A61N 1/056 607/2 |
| 8,005,549 | B2 * | 8/2011 | Boser | A61N 1/05 607/116 |
| 8,175,700 | B2 * | 5/2012 | Johnson | H01F 27/027 607/2 |
| 8,244,373 | B1 * | 8/2012 | Bauer | A61N 1/05 607/116 |
| 2004/0249428 | A1 * | 12/2004 | Wang | A61F 2/90 607/116 |
| 2008/0242964 | A1 * | 10/2008 | Horrigan et al. | 600/377 |
| 2008/0288040 | A1 * | 11/2008 | Eckerdal et al. | 607/127 |
| 2010/0292768 | A1 * | 11/2010 | Sommer | A61N 1/0573 607/116 |
| 2011/0213233 | A1 * | 9/2011 | Stevenson | A61B 5/04 600/373 |
| 2011/0245644 | A1 * | 10/2011 | Stevenson | A61B 5/04 600/372 |
| 2011/0301678 | A1 * | 12/2011 | Alexander | A61N 1/0551 607/116 |
| 2013/0317584 | A1 * | 11/2013 | Stevenson | A61B 5/04 607/116 |

* cited by examiner

LOAD-CARRYING BODY FOR REDUCING TORSIONAL AND TENSILE LOADING ON ELECTRONIC COMPONENTS IN AN IMPLANTABLE MEDICAL ELECTRICAL LEAD

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

*CROSS-REFERENCE TO RELATED APPLICATIONS*

*The present application is a reissue application of application Ser. No. 12/914,048, filed on Oct. 28, 2010, now U.S. Pat. No. 8,244,373, which is a continuation-in-part of application Ser. No. 12/891,292, filed on Sep. 27, 2010, now U.S. Pat. No. 8,437,865, which is a continuation-in-part of application Ser. No. 12/873,862, filed on Sep. 1, 2010, now U.S. Pat. No. 8,224,440, which is a continuation-in-part of application Ser. No. 12/607,234, filed on Oct. 28, 2009, now U.S. Pat. No. 8,175,700, which is a continuation-in-part of application Ser. No. 11/558,349, filed on Nov. 9, 2006, now U.S. Pat. No. 7,945,322, said application Ser. No. 12/873,862 is a continuation-in-in-part of application Ser. No. 11/943,854, filed on Nov. 21, 2007, now U.S. Pat. No. 7,853,325.*

*The present application claims priority from provisional application Ser. No. 61/256,658, filed on Oct. 30, 2009, provisional application Ser. No. 61/303,109, filed on Feb. 10, 2010, provisional application Ser. No. 61/243,643, filed on Sep. 18, 2009, provisional application Ser. No. 61/314,676, filed on Mar. 17, 2010, and provisional application Ser. No. 61/245,720, filed on Sep. 25, 2009.*

FIELD OF THE INVENTION

The present invention generally relates to implantable medical electrical leads. More particularly, the present invention relates to an implantable medical electrical active fixation lead configured to reduce or eliminate torsional and tensile loading on feed-thru pins, insulators, and brazed joints.

BACKGROUND OF THE INVENTION

A wide assortment of implantable medical devices are presently known and in commercial use. Such devices include cardiac pacemakers, cardiac defibrillators, cardioverters, neurostimulators, and other devices for delivering and/or receiving electrical signals to/from a portion of the body. Sensing and/or stimulating leads extend from the associated implantable medical device to a distal tip electrode or electrodes in contact with body tissue. These electrodes should be securely fixed to the tissue to facilitate electrical stimulation or sensing by the implantable medical device.

In order to work reliably, leads need to be stably located adjacent to the tissue to be stimulated or monitored. One common mechanism for accomplishing this has been the use of a fixation helix, which exits the distal end of the lead and is screwed directly into the body tissue. The helix itself may serve as an electrode or it may serve as an anchoring mechanism to fix the position of an electrode mounted to or forming a portion of the lead itself. This is known in the art as active fixation. The fixation helix electrode and lead must be resistant, during and after implantation, to damage both through torsion and tension. The reason they must be resistant to torsion is that during the initial implant, the physician applies a torque tool to the proximal end, which he then twists in order to drive the helix screw into body tissue. If the physician does not achieve a desired capture level or desired pacing site, the physician may unscrew the helix and then pull on the lead to re-position it at a different site. This pull force creates a tension on the lead and its associated distal tip electrode components. Another reason that tensile force may be applied to the lead is during lead extraction surgeries. Generally, lead extraction surgery is done to replace a damaged lead or one that has poor insulation resistance.

One problem associated with implanted leads is that they act as an antenna and tend to pick up stray electromagnetic signals from the surrounding environment. This is particularly problematic in an MRI environment where the currents which are imposed on the leads can cause the leads to heat to the point where tissue damage is likely. Moreover, the currents developed in the leads during an MRI procedure can damage the sensitive electronics within the implantable medical device. Bandstop filters, such as those described in U.S. Pat. No. 7,363,090 and U.S. 2007/0112398 A1, which are herein incorporated by reference, reduce or eliminate the transmission of damaging frequencies along the leads while allowing the desired biological frequencies and pacing pulses to pass efficiently through. However, when implanting the medical electrical lead, stress can be applied directly to the bandstop filter or electrical components either through torsion or tensile loads. Such loads are created because the electrical components are mechanically connected to the lead, and may damage the electrical components during the implanting procedure. This is obviously a negative occurrence which should be avoided.

Accordingly, there is a need for an implantable medical lead having an electronic component such as a low pass filter or bandstop filter, wherein the torsional and tensile loads applied to the electronic component during implantation are reduced or even eliminated. The present invention fulfills these needs and provides other benefits.

SUMMARY OF THE INVENTION

The present invention resides in a load-carrying body for reducing torsional and tensile loading on electronic components in an implantable medical electrical lead. An electronic component is disposed in-line with the implantable medical lead, and has a proximal end conductively coupled to a lead conductor and a distal end conductively coupled to a lead electrode. A casing for the electronic component is mechanically coupled to the lead so as to isolate the electronic component from torque or tensile loads applied to the lead, the lead electrode or both.

In order to isolate the electronic component from torque or tensile loads applied to the lead, the lead electrode or both, a proximal torque coupler is disposed between the lead and the casing, and a distal torque coupler is disposed between the lead electrode and the casing. The casing may include a proximal hermetic seal isolated by the proximal torque coupler from torque or tensile loads applied to the lead. The casing may also include a distal hermetic seal isolated by the distal torque coupler from torque or tensile loads applied to the lead electrode.

The electronic component may comprise a bandstop filter, an electronic switch, a MEMs switch, a diode array, a multiplexer, a pin diode, a capacitor, a resistor, an inductor, an electronic sensor or any combination thereof. The sensor may include a blood gas sensor, a pressure (hemodynamic) sensor, or the like.

The proximal torque coupler includes a proximal pin mechanically attached to the lead conductor and conductively coupled to the lead conductor and the electronic component. A drive shaft may be disposed between the proximal pin and the lead conductor. The distal torque coupler includes a distal pin mechanically attached to the lead electrode and conductively coupled to the lead electrode and the electronic component.

A collar may be disposed at a distal end of the implantable medical electrical lead. In such case, the casing is typically disposed within the collar and is translatable along a longitudinal axis of the collar. A seal is typically disposed between the casing and the collar for preventing passage of ionic fluid into the lead through its distal end. The seal may be disposed at a distal end, a proximal end, or along the middle of the casing. In various configurations, the seal may be fixed relative to the casing or, alternatively, fixed relative to the collar.

The seal prevents ingress of bodily fluids inside the lead body and electrically isolates the electronic component and the pins of the casing. Isolating the pins extending in non-conductive relationship with the casing from each other is very important. For example, a bandstop filter may present an impedance of 2000 ohms at resonance. This desirably impedes the flow of MRI induced RF current into body tissue through the electrode. However, if the pins are not isolated from each other, a parallel path through body fluids (ionic fluid) could result in a parallel path of approximately 80 ohms. This conduction through surrounding fluid would degrade the MRI RF signal attenuation of the bandstop filter. Accordingly, it is important to be able to isolate the opposite ends of the pins of the electronic component.

An insulative conformal coating may be disposed about at least a portion of the casing. The conformal coating may comprise a dielectric ceramic coating, an alumina or parylene, and may be applied by sputtering, chemical vapor deposition, physical vapor deposition, dipping in or applying a chemical solution. The casing may comprise a dielectric ceramic coating comprised of alumina.

The aforementioned drive shaft may be associated with a proximal pin extending from the casing. This drive shaft may comprise a hollow stylet-receiving rigid tube.

Other features and advantages of the present invention will become apparent from the following more detailed description which illustrate, by way of example, the principles of the invention.

BRIEF DESCRIPTION OF THE DRAWINGS

The accompanying drawings illustrate the invention. In such drawings.

DETAILED DESCRIPTION OF THE PREFERRED EMBODIMENTS

Figure 1:
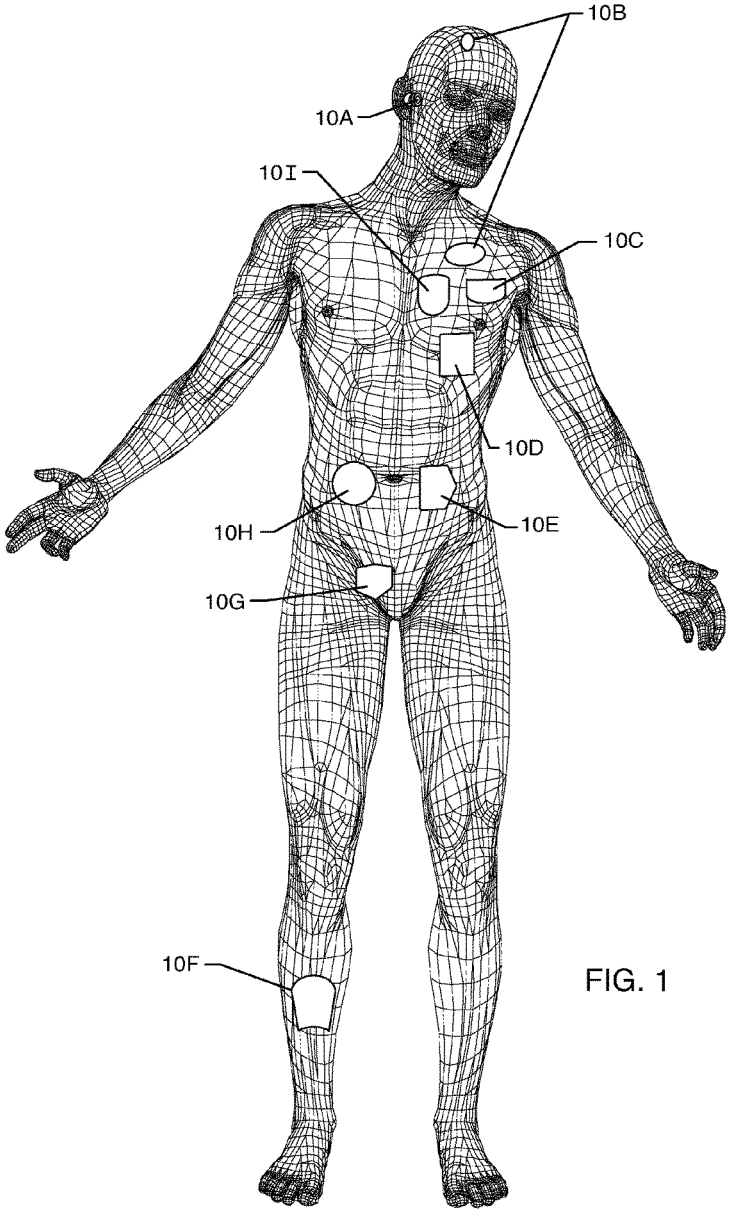
FIG. 1 is a wire-formed diagram of a generic human body showing a number of exemplary implanted medical devices.

FIG. 1 is a wire formed diagram of a generic human body showing a number of implanted medical devices. 10A represents a family of hearing devices which can include the group of cochlear implants, piezoelectric sound bridge transducers and the like. 10B represents a variety of neurostimulators and brain stimulators. Neurostimulators are used to stimulate the Vagus nerve, for example, to treat epilepsy, obesity and depression. Brain stimulators are pacemaker-like devices and include electrodes implanted deep into the brain for sensing the onset of the seizure and also providing electrical stimulation to brain tissue to prevent the seizure from actually occurring. 10C shows a cardiac pacemaker which is well-known in the art. 10D includes the family of left ventricular assist devices (LVAD's), and artificial hearts, including the artificial heart known as the Abiocor. 10E includes an entire family of drug pumps which can be used for dispensing of insulin, chemotherapy drugs, pain medications and the like. 10F includes a variety of bone growth stimulators for rapid healing of fractures. 10G includes urinary incontinence devices. 10H includes the family of pain relief spinal cord stimulators and anti-tremor stimulators. 10H also includes an entire family of other types of neurostimulators used to block pain. 10I includes a family of implantable cardioverter defibrillators (ICD) devices and also includes the family of congestive heart failure devices (CHF). This is also known in the art as cardiac resynchronization therapy devices, otherwise known as CRT devices.

Figure 2:
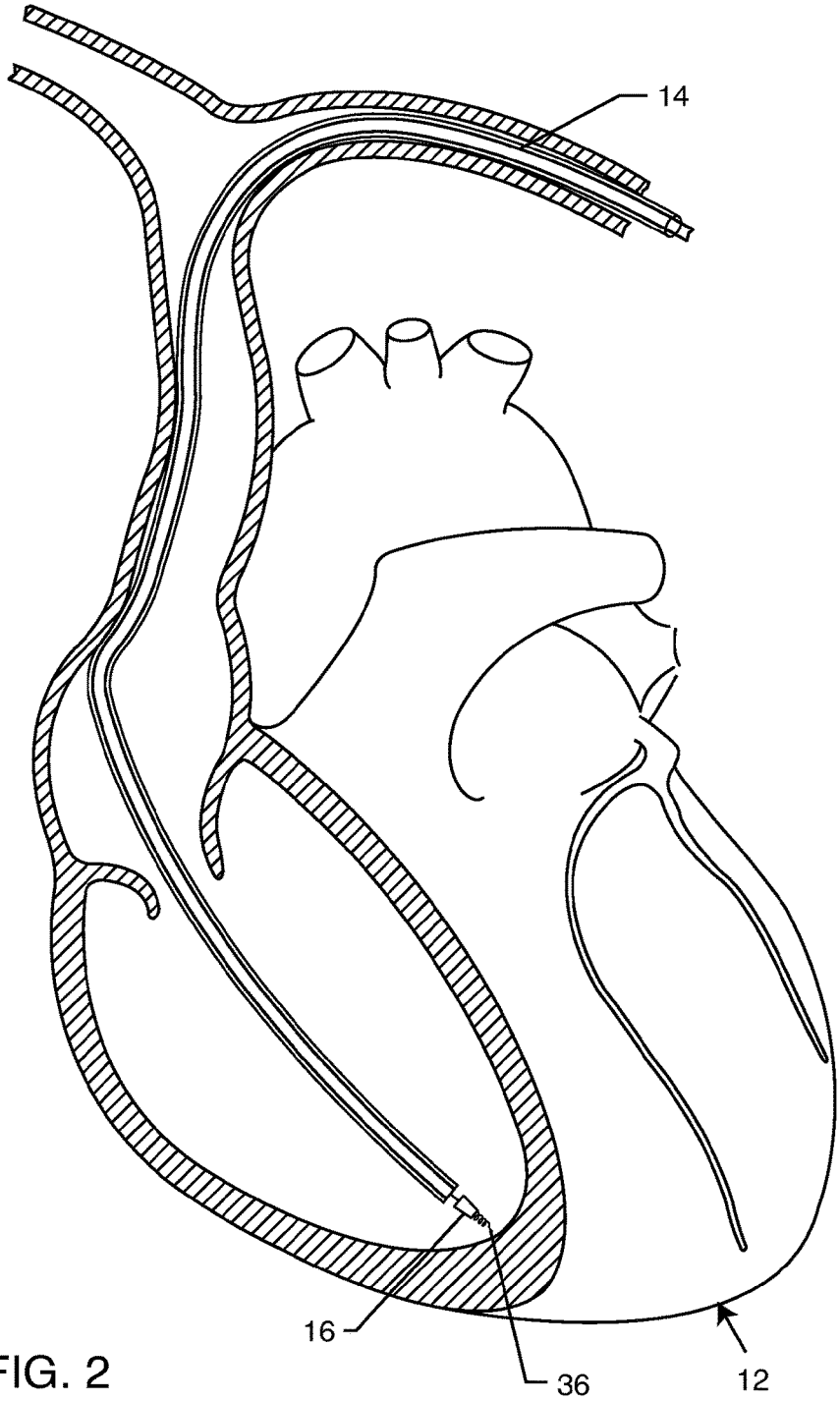
FIG. 2 is a schematic illustration of a human heart with an implanted medical electrical lead.

FIG. 2 is a schematic illustration of a human heart 12 with an implanted medical electrical lead 14. The medical electrical lead 14 includes an electrical or electronic component 16 in series with the active fixation distal helix electrode(s) 36. Once the medical electrical lead 14 is in the desired location, it is typically attached to cardiac tissue with a helical tip 36 (active) or even passive fixation electrode(s) (not shown).

Figure 3:
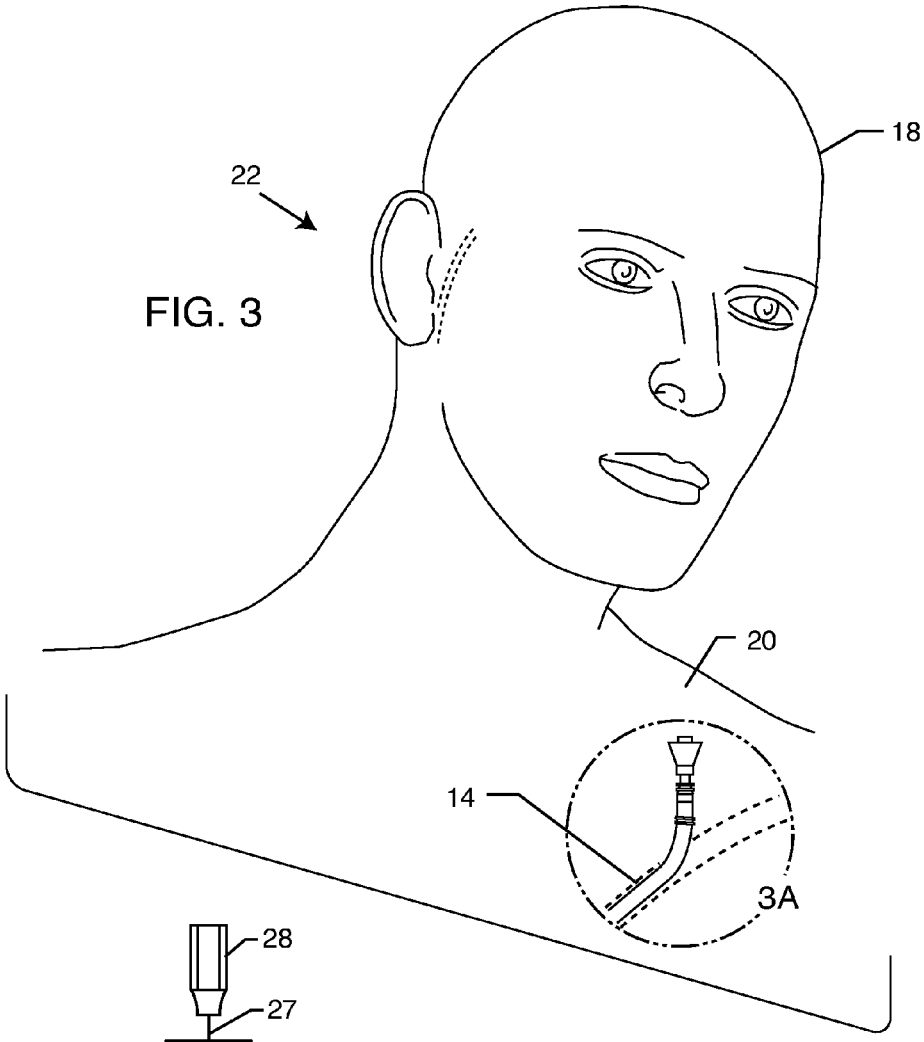
FIG. 3 is an outline illustration of the head and left pectoral region of a patient undergoing implantation of a medical electrical lead.
Figure 3A:
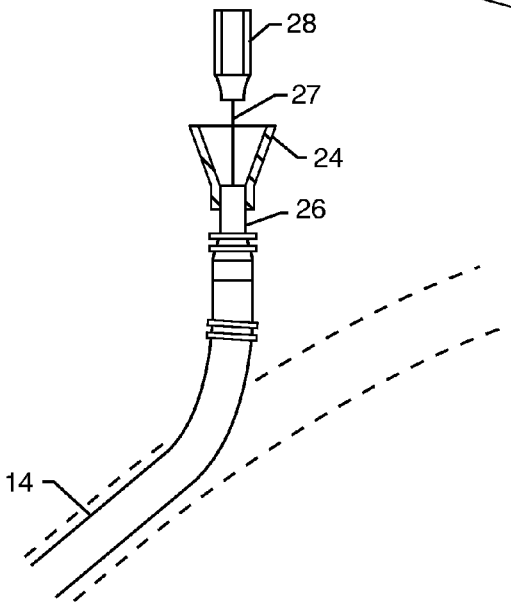
FIG. 3A is an enlarged view of area 3A in FIG. 3.

FIG. 3 is an outline illustration of the head 18 and left pectoral region 20 of a patient 22 undergoing implantation of a medical electrical lead 14. FIG. 3A is an enlarged view of area 3A in FIG. 3. The medical electrical lead 14 is implanted through a venous access in the left (or right) pectoral region 20 of the patient 22 and delivered endocardially through the veins and into the heart using an introducer 24, connector pin 26, guide wire 27, and stylet knob 28.

Figure 4:
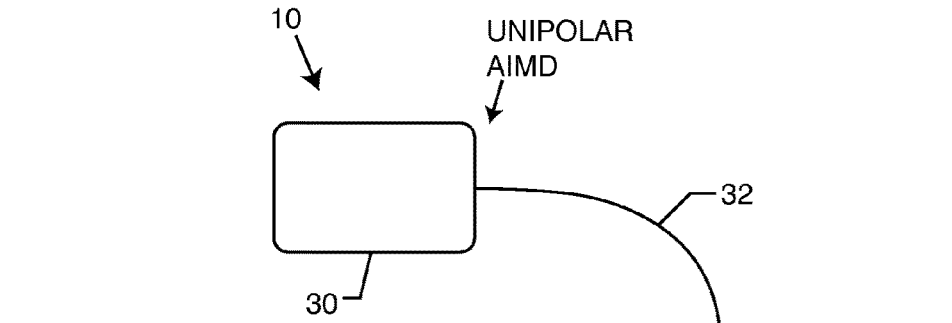
FIG. 4 is a schematic diagram of a unipolar active implantable medical device.

FIG. 4 is a general diagram of a unipolar active implantable medical device (AIMD) 10. The AIMD housing 30 is typically titanium, ceramic, stainless steel or the like. Inside of the device housing 30 are the AIMD electronic circuits. Usually AIMDs include a battery, but that is not always the case. A unipolar lead 32 is routed from the AIMD 10 to a distal electrode 34 where it is embedded in or affixed to body tissue. In the case of a spinal cord stimulator 10H, the distal electrode 34 could be in the spinal cord. In the case of a deep brain stimulator 10B, the distal electrode 34 would be placed deep into the brain, etc. In the case of a cardiac pacemaker 10C, the distal electrode 34 would typically be placed in the cardiac right ventricle.

Figure 5:
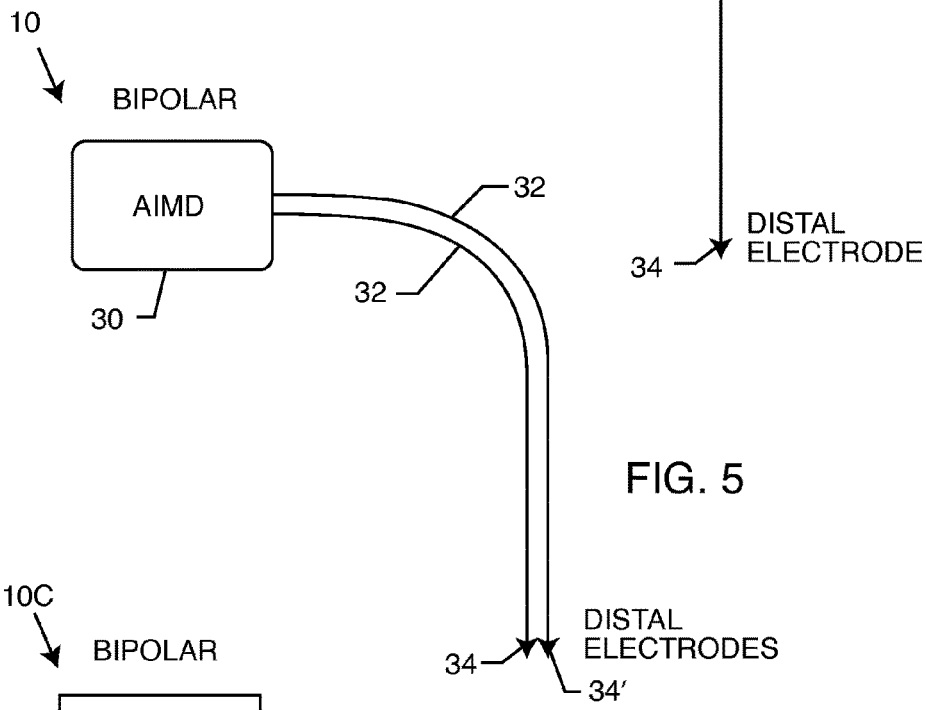
FIG. 5 is a diagram similar to FIG. 4, illustrating a bipolar active implantable medical device.

FIG. 5 is very similar to FIG. 4 except that it is a bipolar system. In this case, the electrical simulation and sensing may be between the two distal electrodes 34 and 34'. In the case of a cardiac pacemaker 10C, this would be known as a bipolar lead system with one of the electrodes known as the distal tip electrode 36 and the other electrode which would float in the blood pool known as the ring electrode 38 (see FIG. 6). In contrast, the electrical tissue simulation and sensing path in FIG. 4 is between the distal electrode 34 through body tissue to the conductive housing 30 of the implantable medical device 10 (the bipolar system of FIG. 5 can be typically programmed into the unipolar mode shown in FIG. 4).

Figure 6:
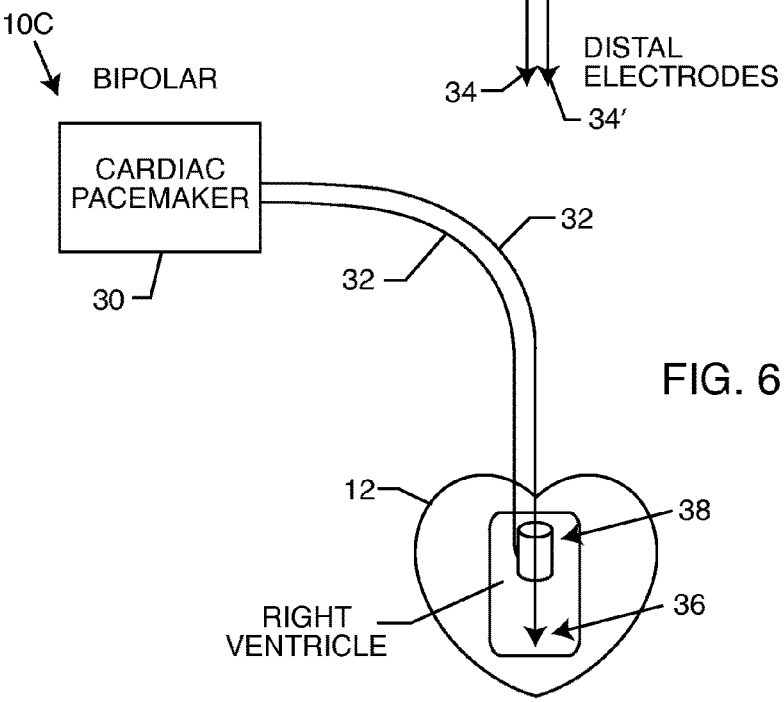
FIG. 6 is a diagram similar to FIGS. 4 and 5, illustrating a biopolar lead wire system with a tip and ring electrode, typically used in a cardiac pacemaker.

FIG. 6 illustrates a single chamber bipolar lead system with a distal tip electrode 36 and ring electrode 38 typically as used in a cardiac pacemaker 10C.

In all of these applications, a patient exposed to the fields of an MRI scanner or other powerful emitter used during a medical diagnostic procedure, could have currents induced in the leads 32 and, in turn, can cause heating by $I^2R$ losses in the lead conductor 32 or by heating caused by current flowing from an electrode 36, 38 into body tissue. If these currents become excessive, the associated heating can cause damage or even destructive ablation to body tissue.

The distal tip electrode 36 is designed to be implanted into or affixed to the endocardial or myocardial tissue of the heart. The ring electrode 38 is designed to float in the blood pool. Because the blood is flowing and is thermally conductive, the ring electrode 38 structure is substantially cooled during MRI scans. In theory, the ring electrode 38 could also touch the myocardial or trabecular tissue and become encapsulated. When electrodes 36 and/or 38 are encapsulated they become thermally insulated by surrounding body tissue and can readily heat up due to the RF pulse currents of an MRI field.

Figure 7:
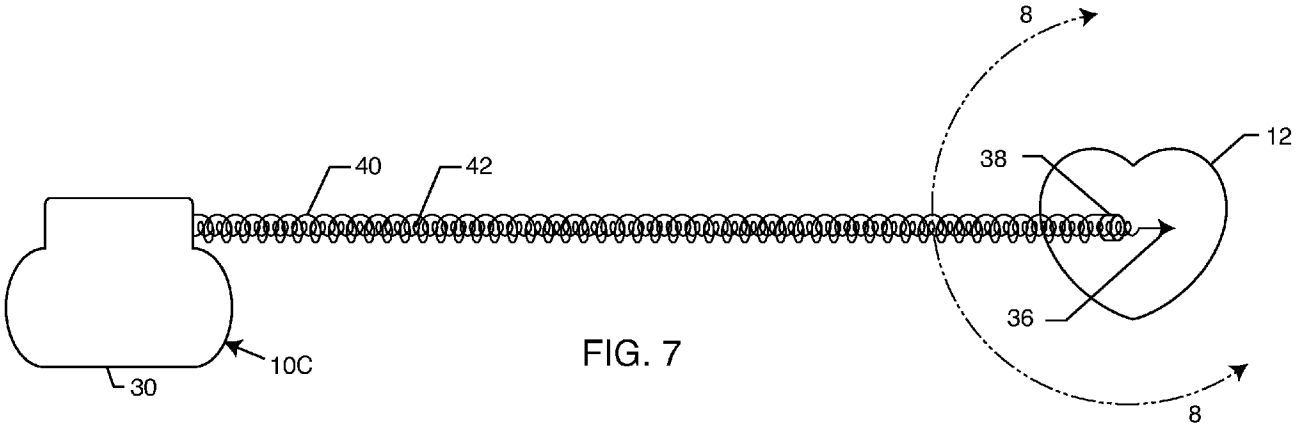
FIG. 7 illustrates a bipolar cardiac pacemaker lead wire showing the tip and ring electrodes.

FIG. 7 illustrates a single chamber bipolar cardiac pacemaker lead wire showing the distal tip electrode 36 and the distal ring electrode 38. This is a coaxial wound system where the ring electrode lead conductor 40 is wrapped around the tip electrode lead conductor 42. There are other types of pacemaker lead systems in which these two conductors lay parallel to one another (known as a bifilar lead system).

Figure 8:
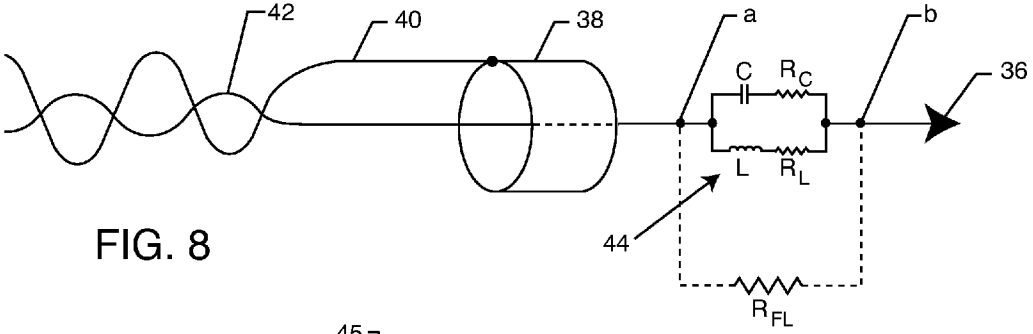
FIG. 8 is an enlarged, fragmented schematic illustration of the area illustrated by the line 8-8 in FIG. 7.

FIG. 8 is a schematic illustration of the area 8-8 in FIG. 7. In the area of the distal tip electrode 36 and ring electrode 38, bandstop filter 44 has been placed in series with the tip electrode conductor 42. The bandstop filter 44 consists of a passive component inductor L in parallel with a capacitor C which is designed to be resonant at an MRI pulsed RF frequency. The resistive losses $R_C$ and $R_L$ of the capacitor and the inductor are carefully controlled such that the bandstop filter 44 has a resulting 3 dB bandwidth to achieve substantial attenuation along a selected range of MRI RF pulsed frequencies. Accordingly, at MRI pulsed frequencies, a very high impedance is presented thereby reducing the flow of undesirable RF current into body tissue. A bandstop filter 44 could also be placed in series with the ring electrode lead wire 40. The bandstop filter 44 shown is exemplary of any type of passive component network (any combination of inductors, resistors or capacitors) that could be used in the present invention. An electronic switch, a MEMS switch as taught by U.S. Pat. No. 6,944,489, a diode array, an electronic switch, an inductor, a multiplexer or any combination thereof, could also advantageously be used with or instead of the bandstop filter 44.

Figure 9:
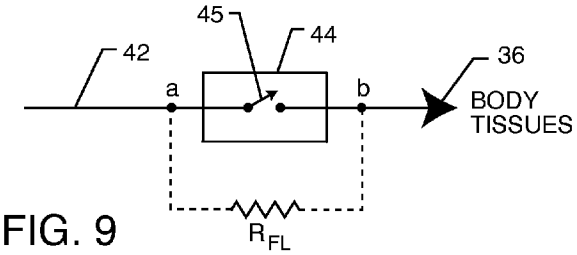
FIG. 9 is a schematic illustration similar to FIG. 8, showing the undesirability of permitting a parallel electrical path through body fluids around an impeding electrical component.

Referring once again to FIG. 8, it is important that the implanted bandstop filter 44 have a high insulation resistance (IR) between points "a" and "b", which are external to the electronic element. In this case, the bandstop filter 44 would provide a high impedance at resonance (above 1000 ohms) to reduce the flow of RF currents induced in the lead into body tissue. However, if both ends of the bandstop filter 44 were exposed to ionic containing fluids (i.e. body fluid), then external conduction paths would occur. Experiments by the inventors have shown that a parallel resistance of 80 ohms could result, which would significantly and undesirably reduce the impedance of the bandstop filter 44 at resonance. This parallel IR is shown in FIGS. 8 and 9 as $R_{FL}$ which represents the conduction through body fluid which would occur from end to end (points a to b) if the bandstop filter 44 were not properly insulated and isolated. For a typical bandstop filter, let's assume that its impedance at resonance at 64 MHz was 2000 ohms. If it undesirably had ionic fluids exposed to its external contacts at points a and b, this would mean that an 80 ohm insulation resistance now appears in parallel with the 2000 ohm impedance. Using the parallel resistance Rp formula wherein $R_P=(R_1R_2)/(R_1+R_2)$ $=(80)(2000)/(2000+80)=76.9$ ohms. This would be disastrous for the operation of the bandstop filter 44. Instead of presenting 2000 ohms at resonance to the MRI pulsed frequency, it would present only 76.9 ohms. This would result in a great deal of RF current flowing through the distal electrode into body tissue which is highly undesirable. It is a feature of the present invention that along with a torque coupler—tensile stress isolator, insulating seals and/or insulating conformal coatings be provided such that this low value of parallel insulation resistance does not occur in parallel with the electronic circuit element. The electronic circuit element of the present invention is not limited to just L-C parallel resonant bandstop filters. It is equally important for inductors, electronic switches, MEMS switches, pin diodes, L-C trap filters, low pass filters, diode arrays, electronic multiplexers, electronic sensors, or any other type of active or passive electronic circuit wherein torque and tensile load protection is needed along with a high insulation resistance is needed from one end of it to the other end of it, as described as points a and b in FIGS. 8 and 9.

FIG. 9 is very similar to FIG. 8 except that the electronic device 44, in this case, is an electronic switch 45 which is shown in the open position. The electronic switch 45 can actually consist of a pin diode, a MEMS switch, an electronic switch, an electronic sensor, or even a diode array. It is shown in the open position indicating that it's in the MRI compatible position. In other words, MRI RF currents induced onto lead 42 would be unable to flow through distal electrode 36 into body tissue and potentially damage said body tissues.

Figure 10:
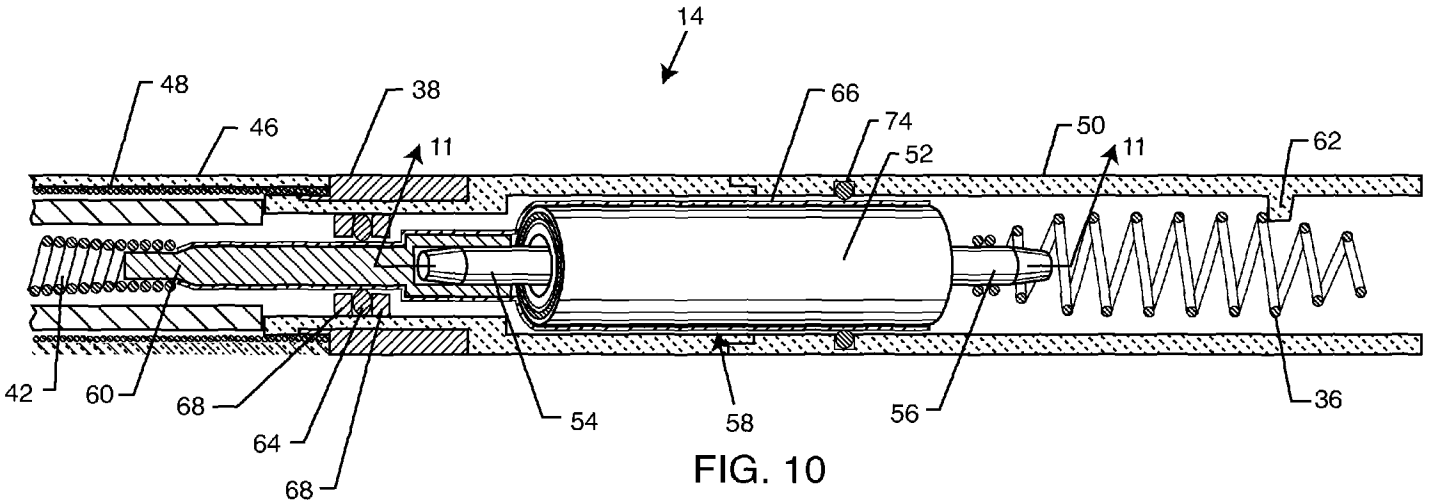
FIG. 10 is a sectional view of an exemplary medical electrical lead embodying the present invention.

FIG. 10 illustrates an exemplary lead 14 which embodies a lead body 46, a coaxial conductor 48 for the ring electrode 38, a coaxial conductor 42 for the tip (active fixation helix) electrode 36, a collar 50, and the translatable casing 52 which houses electronic components. The translatable casing 52 includes a pin 54 and a pin 56. The translatable casing 32 is optionally hermetically sealed at one or both ends. The pin 54 is electrically and mechanically connected to the tip electrode lead wire conductor 42 and the pin 56 is attached to a distal helix electrode 36. The distal helix electrode 36 is also known as an active fixation electrode. The pin 54, the casing 52, and the pin 56 all form what is defined herein as a casing subassembly 58. This is further illustrated in FIG. 11, which shows the cross-section of an inductor L and a capacitor C inside casing 52, which are physically disposed in series, but are electronically connected in parallel to form an L-C resonant bandstop filter 44. This is further described in U.S. 2010/0100164, which is incorporated herein by reference.

Referring once again to FIG. 10, there will typically be a laser weld (not shown) electrically and mechanically connecting the tip conductor 42 to a conductive drive shaft 60, there is also a laser weld (not shown) connecting the casing pin 56 to the distal tip electrode 34. During transvenous insertion, the active fixation helix tip 36 is retracted (as shown) so that it will not stab or poke into body tissues during endocardial lead insertion. When the physician has positioned it in the desirable location (perhaps inside the cardiac right ventricle), then the physician takes a special torque tool and twists the proximal end of lead body 46 which causes the entire conductor 42 and drive shaft 60 to rotate. As the casing 52 and distal helix electrode 36 [rotates, it] *rotate, helix electrode* engages a guide 62 which causes the helix 36 to extend and screw into body tissue. The guide 62 may be formed as part of the collar 50 and engages the tip electrode 36 when the tip conductor 42 is rotated. The rotation causes the helical tip electrode 36 to rotate within the collar 50 and thereby translate in a forward manner. At the same time the tip electrode 36 is advancing relative to the collar 50, it is engaging with body tissue by being screwed directly into the tissue to thereby form an attachment. The tip electrode 36 can be rotated in the opposite direction by rotating the tip conductor 42 and thereby disengaged from the tissue for removal and/or reattachment at a different location. This is a method of active affixation which is well known in the art.

An O-ring 64 is disposed on the proximal end of and subassembly 58. In this case, the seal 64 is only to prevent the intrusion of ionic containing body fluids into the interior of lead body 46. In this case, a conformal coating 66 is disposed over the exterior of the casing 52 and all the way over the pin 54 and even over a portion of a conductive drive shaft 60. The conformal coating 66 may be a material for electrical isolation and/or also aid in reducing friction. The conformal coating 66 may also be a dielectric ceramic coating that can be applied in a multitude of ways, such as by sputtering, chemical vapor deposition, physical vapor deposition, or dipping in a chemical solution. The conformal coating 66 may also be made of a variety of materials sufficient to provide insulation, such as alumina. In another exemplary embodiment and to provide further electrical isolation, the casing 52 can also be manufactured as a ceramic tube, and also from materials such as alumina. It is to be understood that such a ceramic tube casing 52 can be used with or without the conformal coating 66.

The lead tip conductor 42, the casing sub-assembly 58 and the distal helix 36 are shown in the retracted position. As the helix is extended, the conformal coating 66 on the inside diameter of seal 64 will slide back and forth as it is part of the drive shaft 60. This provides a high degree of electrical resistance or isolation between the terminal pins 54 and 56 such that undesirable currents do not flow through body fluids from end to end outside of the electronic component casing 52. Seal supports 68 abut the seal 64 on both ends and fix the seal 64 in place. The seal supports 68 can be made from a range of materials, including but not limited to a polymer, polyurethane, metal, elastomer, ceramic, composite or any other suitable material.

Figure 11:
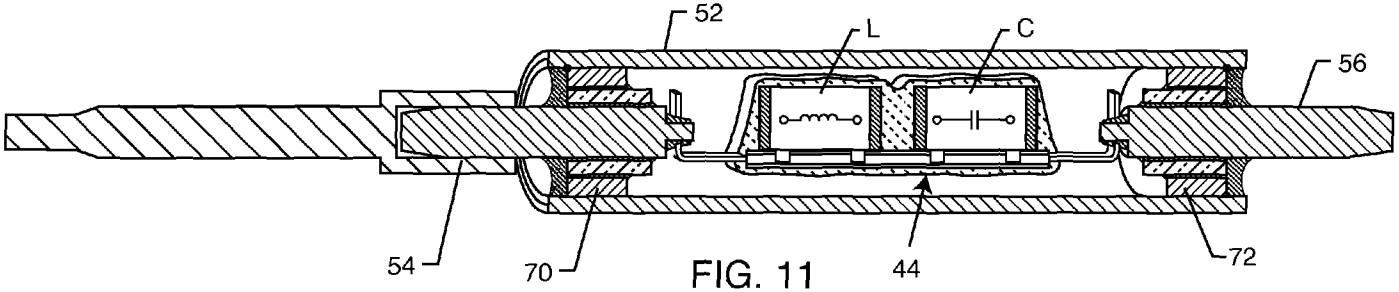
FIG. 11 is an enlarged sectional view of the area illustrated by the line 11-11 in FIG. 10.

FIG. 11 is generally taken from section 11-11 of FIG. 10. Shown is the interior of the translatable casing 52 illustrating bandstop filter components L and C. Terminal pins 54 and 56 extend in non-conductive relationship with the translatable casing 52. Hermetic seals 70 and 72 are shown which form a hermetic seal between the pins 54 and 56 and the translatable casing 52. This protects the inductor L and capacitor C (or other electronic components) from intrusion of body fluids. It is well known in the art that intrusion of moisture, body fluids or other contaminants can cause electronic circuits to short out. It is not an absolute requirement that the translatable casing 52 be hermetically sealed. Electronic components, such as inductor L and capacitor C components, could be utilized that are inherently non-toxic and biocompatible. Components for direct body fluid exposure are described in U.S. Pat. No. 7,535,693 the contents of which are hereby incorporated by reference. However, in the case where there are hermetic seals 70, 72, it is important that the hermetic seals be protected from damage due to excessive torque or tensile loads. In the case where there are no hermetic seals, it's even more important that delicate electronic components be protected from damaging torque or tensile stresses.

The present invention is applicable to any type of active or electronic circuits that may be disposed in or adjacent to a translatable electronic casing 52. The flexible seal 64 of FIG. 10 prevents the entrance of ionic body fluids into the inside of the lead body 46. The seal 64 can be formed in a multitude of ways appreciated by those skilled in the art, such as multiple wipers, o-rings, thin disks or sheets, and various molded profiles. See, for example, U.S. application Ser. No. 12/873,862, the contents of which are incorporated herein.

There is a secondary optional O-ring seal 74 as shown in FIG. 10. The O-ring seal 74 is disposed between the inside diameter of the lead collar 50 and the outside diameter of the electronic component casing 52. The purpose of seal 64 and the O-ring seal 74 is to ensure that ionic body fluids cannot be disposed across the important electrical path between pins 54 and 56. Ionic body fluids could represent a parallel path as low as 80 ohms. Over time, due to bulk permeability, body fluids will penetrate into the interior of the lead body 46. However, this is an osmotic type of action. The resulting fluids that would occur over long periods of time inside the lead body 46 would be distilled and free of ionic contaminants (de-ionized). This means that they would be less conductive of high frequency electrical signals from one end to the other of the electronic component casing 52. The presence of optional O-ring 74 is desirable in that it also presents a high impedance to such a parallel circuit path. The casing 52 may also have a conformal insulative coating 66 for further electrically isolating terminals 54 and 56 such that a parallel path through body fluid is further impeded. The insulative coating may be formed from any suitable material, such as a dielectric material, including, but not limited to parylene, ETFE, PTFE, polyamide, polyurethane and silicone. It will be understood that the exemplary embodiment of FIG. 10 may work with or without such coatings.

Figure 12:
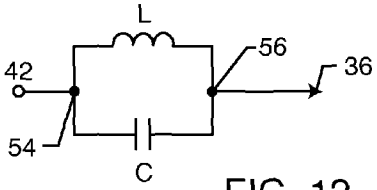
FIG. 12 is an electrical schematic diagram of the bandstop filter illustrated in FIG. 11.

FIG. 12 is an electrical schematic illustration of the bandstop filter illustrated in FIG. 11.

Figure 13:
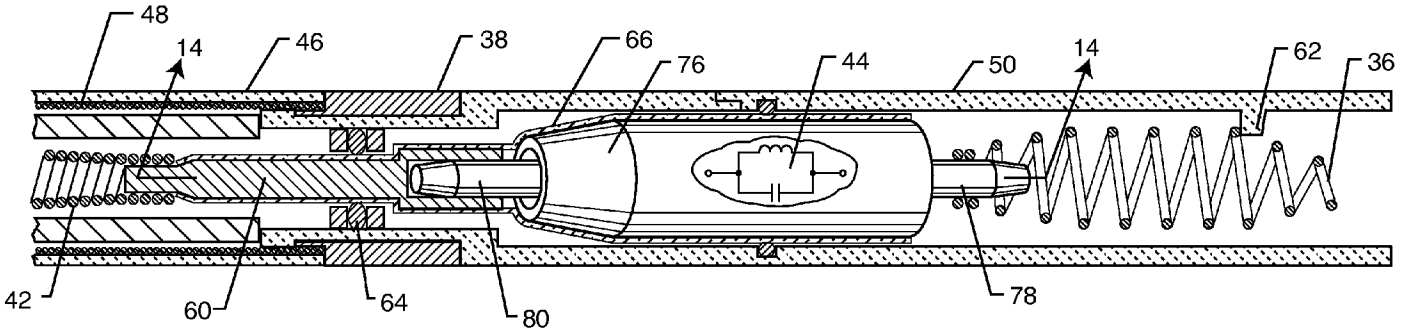
FIG. 13 is a sectional view similar to FIG. 10, showing an exemplary load carrying body embodying the present invention.

FIG. 13 is a perspective illustration of an exemplary unitary torque coupler 76 embodying the present invention. The torque coupler 76 is made of a rigid and non-conductive material. The form of the torque coupler 76 may vary and be formed to match the medical electrical lead's 46 collar 50. A helical electrode tip 36 is attached to the distal torque coupler pin 78. A proximal torque coupler pin 80 is attached to drive shaft 60. Torque and tensile loads applied to the lead 46 are transmitted through the unitary torque coupler 76 while not being transmitted within the electronic components 44 located inside. The torque coupler 76 also protects the mechanically sensitive hermetic seals 70 and 72.

Figure 14:
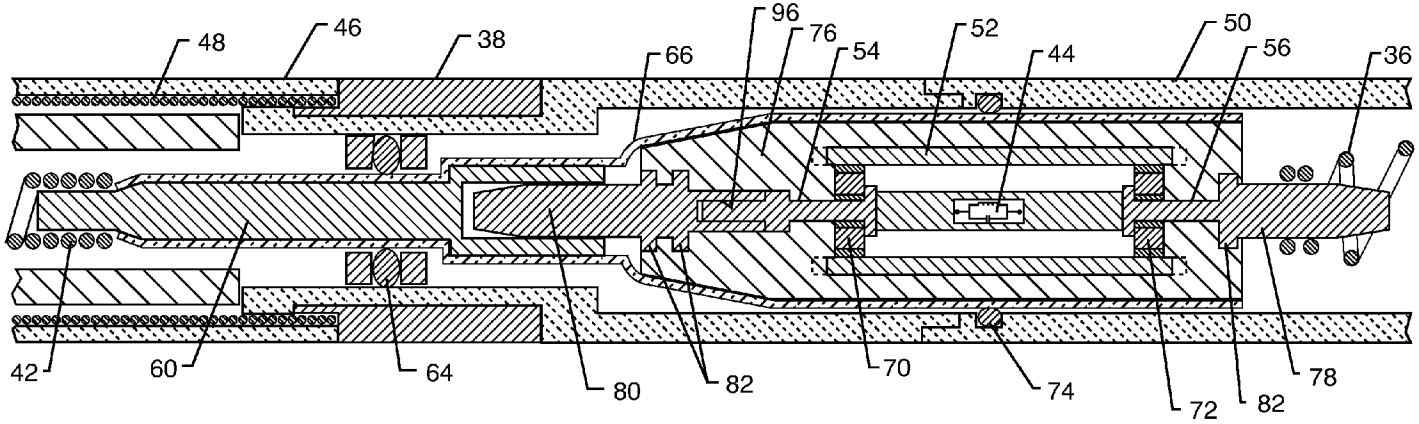
FIG. 14 is an enlarged sectional view taken generally along the line 14-14 of FIG. 13.

FIG. 14 is a sectional view taken from section 14-14 of FIG. 13. As was previously mentioned, the torque coupler 76 is of a rigid and insulative material. It has sufficient strength properties to transmit torque and tensile loads thereby protecting the casing 52 of the electronic module 44. There is a unique coupling mechanism provided by the proximal torque coupler pin 80, which is generally electrically and mechanically attached to proximal pin 54 either by laser welding, brazing of the like. In order to mechanically grasp and adhere to the material of the torque coupler 76, it may have one or more disc-like rings 82 in order to increase its surface area. The rings may have sprocket spokes to lock it to the unitary torque coupler. In general, there is more torque on the proximal side than on the distal side. Accordingly, in the preferred embodiment as shown in FIG. 14, there would be two friction rings 82 on the proximal side and only one on the distal side. The casing 52 is hermetically sealed by hermetic seals 70 and 72. The unitary torque coupler 76 not only protects the delicate electronics 44 inside of the casing 52, but it also protects the delicate hermetic seals 70 and 72. An optional overall insulative coating 66 may be applied. The torque coupler 76 may be formed by a mold into which a biocompatible epoxy is poured and then later cured into a hard state.

During implantation by a physician, the lead body 46 is held in place while the center conductor 42 is rotated using a physician torque tool. As the entire assembly rotates, it is pushed forward by guide 62 which causes the distal helix end 36 to protrude and screw into body tissue. The torque that is applied to the lead conductor 42 is transmitted to drive shaft 60 and in turn to the proximal torque coupler pin 80. The torque is then transmitted mostly into the rigid body of the torque coupler 76 itself thereby bypassing pins 54 and 56. The torque that is transmitted by the torque coupler 76 is further transmitted to the distal torque coupler pin 78. This arrangement, importantly, protects the casing 52, the electronics 44 and the sensitive hermetic seals 70 and 72.

Figure 15:
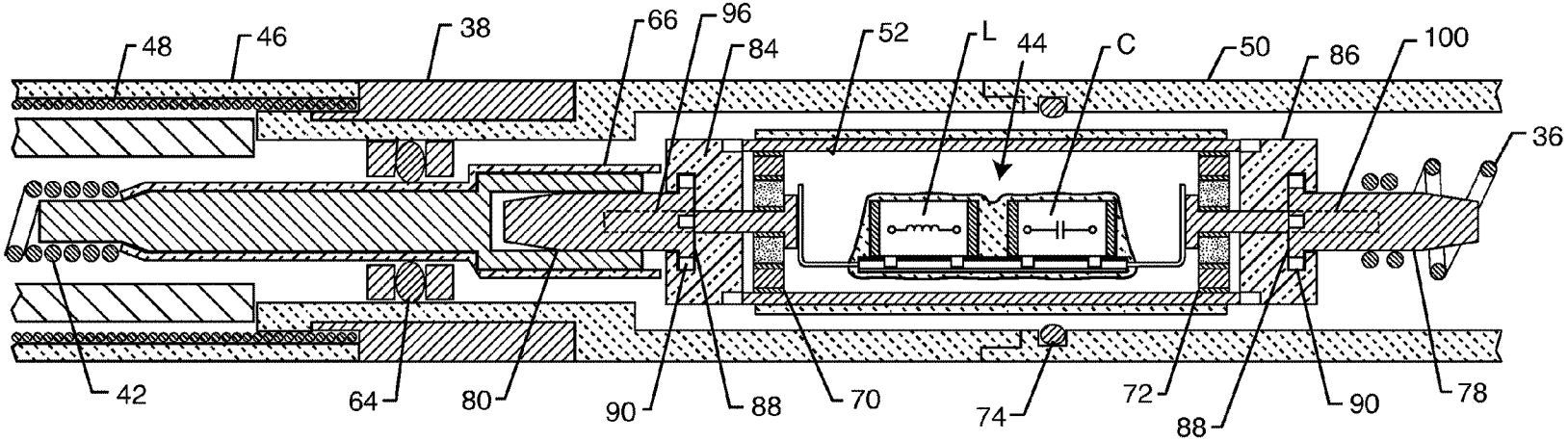
FIG. 15 is a sectional view similar to FIG. 14, showing an alternative configuration.

FIG. 15 shows an alternate torque coupler arrangement. In this case, the torque coupler is divided into two discrete torque couplers, one consisting of a proximal torque coupler 84 and the other consisting of a distal torque coupler 86. In this case, the torque couplers 84, 86 are also of a rigid insulative material. They could be poured in place, such as a non-conductive thermal-setting epoxy or polyimide. They could also be pre-machined from hard plastics, ceramics or the like. In addition, ceramic powders could be pressed into a fixture and then sintered at high temperature in order to make a rigid non-conductive torque coupler.

Each of the distal and proximal torque coupler pins 78 and 80 includes a locking sprocket 88. Similarly, each of the proximal and distal torque couplers 84 and 86 include a locking sprocket-receiving recess 90 configured for receiving a respective locking sprocket 88 therein. These features are better illustrated in FIG. 16, which also shows that the proximal and distal torque couplers 84 and 86 also have a castle parapet configuration 92 on one side for mating reception with a similar castle parapet structure 94 provided on respective ends of the casing 52. In this case, the casing 52 is of a strong and rigid material such that it will not deform during application of torsional loads. These gear/sprocket-like features of the torque couplers 84, 86, torque coupler pins 78, 80 and the casing 52 prevent the torque couplers 84 and 86 from slipping relative to the casing 52 and the respective pins 78 and 80 while under load. In a preferred embodiment, an adhesive (not shown) would be applied to the sprocket 86 engagement surfaces 90 and 92 so that the entire system would be also resistant to tensile loads. In other words, tensile and torque loads applied to the pins 78 and 80 are transmitted through the torque couplers 84 and 86 directly to the casing 52, thereby isolating the electrical components 44 from such torque or tensile loads.

Figure 16:
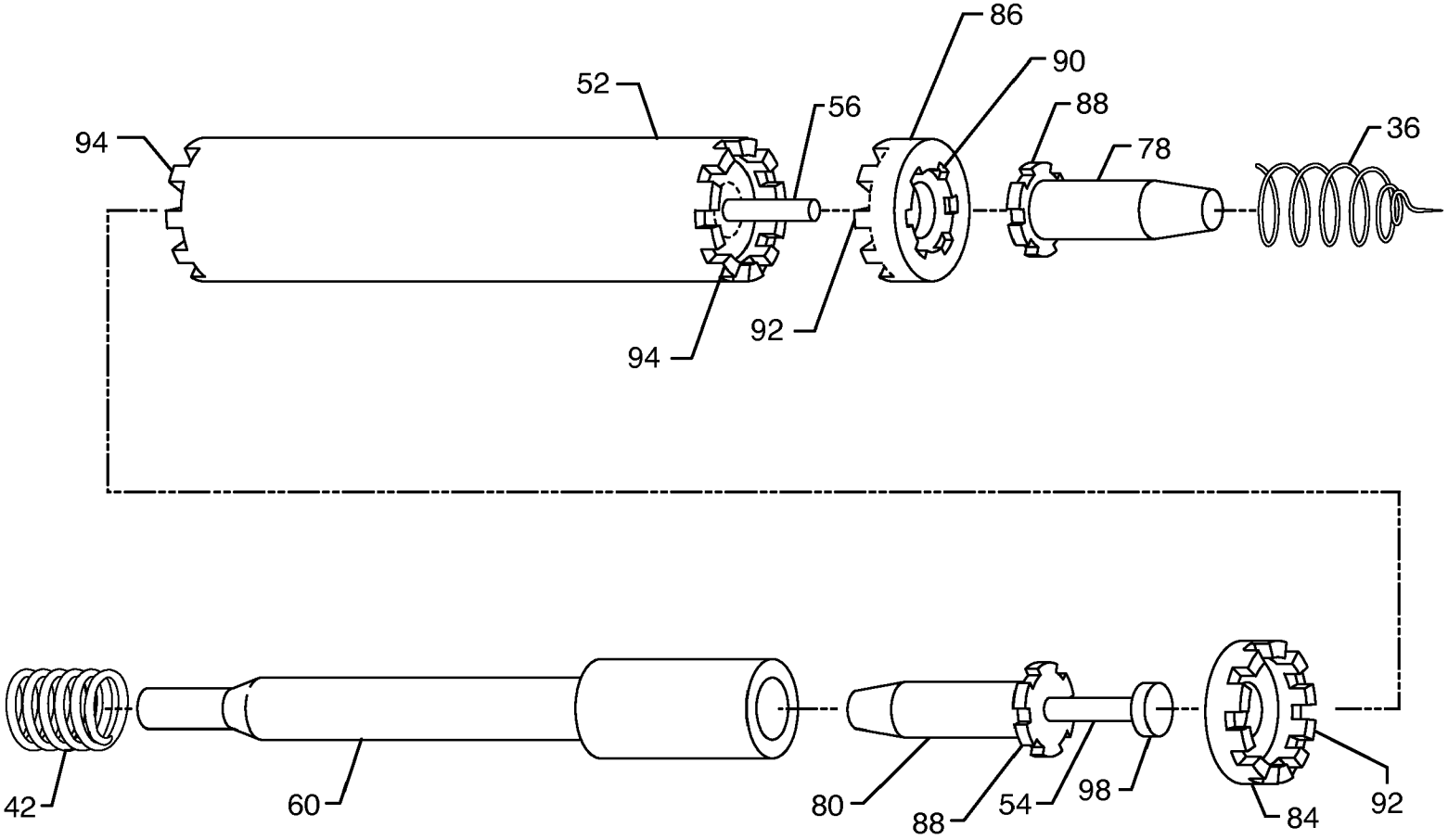
FIG. 16 is an exploded perspective view of the assembly of FIG. 15.

FIG. 16 is an exploded view of various components disposed within the lead body 46 and the collar 50, from FIG. 15. Beginning on the left hand or proximal side one can see the lead tip conductor 42 which attaches to the conductive drive shaft 60. The conductive drive shaft 60 (which is optional) is secured by welding, brazing or the like, to the proximal torque coupler pin 80. The torque coupler pin 80 includes a locking sprocket 88 configured for locking reception within the locking sprocket recess 90 of the proximal torque coupler 84. The proximal pin 54 is fixed within a pin receiving recess 96 provided within the proximal torque coupler pin 80 (see FIG. 15). The distal end of the pin 54 includes a head 98 to which the electronic component (bandstop filter 44) is conductively coupled. Similarly, the distal pin 56 is disposed within a pin receiving recess 100 (FIG. 15) provided within the distal torque coupler pin 78 and is fixed in place by means of a weld or the like. A distal pin 56 extends through the distal hermetic seal 72, and includes a head 102 which is conductively coupled to the electronic components (bandstop filter 44) disposed within the casing 52. A sprocket 88 is configured for locking reception within the locking sprocket recess 90 provided in the distal torque coupler 86. The tip electrode 36 is fixed to the distal torque coupler pin 78. Importantly, the proximal and distal torque couplers 84 and 86 each include a castle parapet structure 92 that mates with a corresponding castle parapet structure 94 provided on respective ends of the casing 52. As described previously, this structure ensures that the electrical components within the casing 52 are isolated from torque or tensile loads applied to the lead 14, the lead electrode 36, or both.

Figure 17:
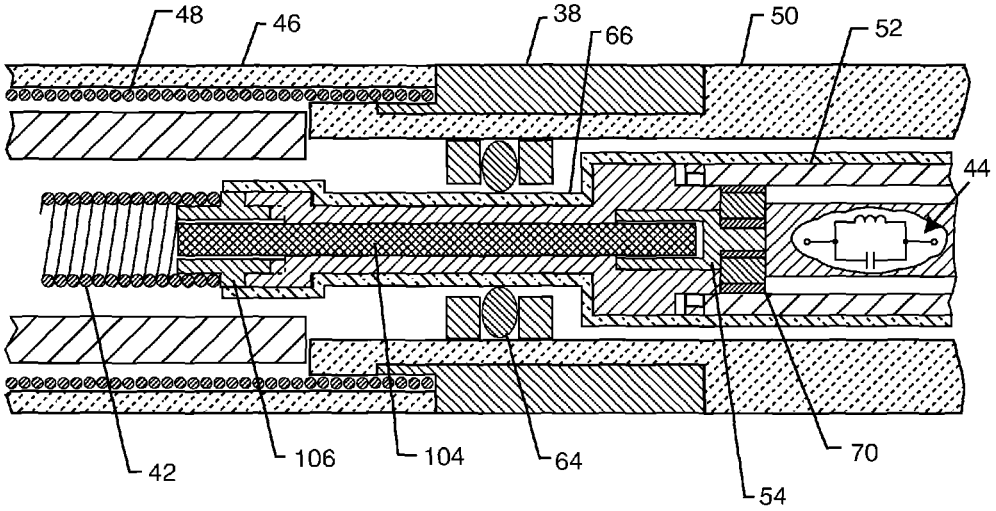
FIG. 17 is a sectional view similar to FIG. 15, of another exemplary load carrying body embodying the present invention.

FIG. 17 is a sectional view similar to FIGS. 14 and 15. In this case, the pin 54 has a unique cup shape to receive a conductive shaft 104. This shaft 104 is attached to a ferrule 106 which is in turn connected to the lead conductor 42. Since it is very important that torque not be transmitted from lead conductor 42 through the shaft 104 to the pin 54, hermetic terminals this small generally consist of a single sapphire ceramic or an alumina ceramic. Metallization is attached to these pins by first sputtering and then gold brazing. An elongated torque coupler 108 is connected to the ferrule 106 and is in turn connected to the parapet structure 94 that is located on the end of the casing 52 in order to lock it in place. The elongated torque coupler 108 operates in accordance with the present invention so that torque or tensile loads that are transmitted via the lead conductor 42 bypass the conductive shaft 104 and the hermetic seal 70.

From the foregoing, it will be appreciated that the present invention relates to a lead body adapted for in-vivo implantation in a living subject, said lead body comprising a proximal end configured for electrical and mechanical connection to a therapy delivery or monitoring device, and a distal end which is connected to a translatable active fixation electrode in contact with body tissues. The distal end of the lead body encompasses a collar in which a casing is enclosed. The casing includes electronic components which can either be active or passive. One or both ends of the casing 52 (or alternatively the entire casing), is protected by a novel torque coupler. The torque coupler protects either the sensitive hermetic seals of casing 52 or the internal electronic components 44 from damage due to torque applied to torque or tensile loads applied to lead conductor 42, the tip electrode 36, or both. In a preferred embodiment, the casing includes a passive inductor and capacitor element configured to form a parallel resonant L-C bandstop filter. The casing is translatable within the collar, which causes a distal helix electrode to rotate and literally be screwed into body tissue. The helix electrode is also known as an active fixation electrode. The casing is part of a casing assembly which includes a seal which is disposed between the casing assembly and the collar whereby the seal prevents passage of ionic body fluids in the living subject into the lead body fluid distal end. Conformal coatings can be placed over the translatable casing so that high resistance path is provided from one end of the active or passive electronic circuit to the other. The active or passive electronic circuit can include L-C bandstop filters, L-C trap filters, low pass filters, electronic sensors, passive or active electronic switches, MEMS switches, pin diode switches, non-linear circuit elements, such as diodes and the like. The conformal coating may be a dielectric material for electrical isolation and/or also aid in reducing friction.

Although several embodiments have been described in detail for purposes of illustration, various modifications may be made to each without departing from the scope and spirit of the invention.

What is claimed is:

1. [A load-carrying body for reducing torsional and tensile loading on electronic components in an] *An* implantable medical electrical lead, comprising:

*a*) *a lead conductor extending from a proximal lead conductor end to a distal lead conductor end, wherein the proximal lead conductor end is connectable to an implantable pulse generator;*

*b*) *an electrode configured for contact with body tissue;*

*c*) an electronic component [disposed in-line with an implantable medical electrical lead, the electronic component] having a proximal *electronic component* end conductively *and physically* coupled to [a] *the distal* lead conductor *end,* and a distal *electronic component* end conductively *and physically* coupled to [a lead] *the* electrode; and

*d*) a [casing for] *rigid, torque bearing member supporting* the electronic component, *wherein a proximal end of* the [casing being] *torque bearing member is* mechanically*, but not conductively* coupled to the *distal* lead *conductor end, and a distal end of the torque bearing member is mechanically, but not conductively coupled to the electrode, and*

[so as to isolate] *e*) *wherein the torque bearing member isolates* the electronic component from torque or tensile loads applied to the lead *conductor*, the [lead] electrode, or both.

2. The [load-carrying body] *implantable medical electrical lead* of claim 1, [including] *wherein* a proximal torque coupler [disposed] *is mechanically and conductively coupled* between *and to* the lead *conductor* and the [casing] *electronic component*.

3. The [load-carrying body] *implantable medical electrical lead* of claim 2, wherein [the casing includes a proximal hermetic] *a* seal [isolated by] *conductively isolates* the proximal torque coupler from *the* torque [or tensile loads applied to the lead] *bearing member*.

4. The [load-carrying body] *implantable medical electrical lead* of claim 2, wherein the proximal torque coupler includes a proximal pin mechanically [attached to the lead conductor] and conductively coupled to the lead conductor and the electronic component.

5. The [load-carrying body] *implantable medical electrical lead* of claim 4, [including] *wherein* a drive shaft *is* disposed between the proximal pin and the lead conductor.

6. The [load-carrying body] *implantable medical electrical lead* of claim 1, [including] *wherein* a distal torque coupler [disposed] *mechanically and conductively couples* between *and to* the [lead] electrode and the [casing] *electronic component*.

7. The [load-carrying body] *implantable medical electrical lead* of claim 6, wherein [the casing includes a distal hermetic] *a* seal [isolated by] *conductively isolates* the distal torque coupler from *the* torque [or tensile loads applied to the lead electrode] *bearing member*.

8. The [load-carrying body] *implantable medical electrical lead* of [any of claims] *claim* 1[-6], wherein the electronic component [comprises] *is selected from the group consisting of* a bandstop filter, an electronic switch, a MEMs switch, a diode array, a multiplexer, a pin diode, a capacitor, a resistor, an inductor, an electronic sensor, [or any combination] *and combinations* thereof.

9. The [load-carrying body] *implantable medical electrical lead* of claim 6, wherein the distal torque coupler includes a distal pin mechanically [attached to the lead electrode] and conductively coupled to the [lead] electrode and the electronic component.

10. The [load-carrying body] *implantable medical electrical lead* of [any of claims] *claim* 1[-6], [including] *wherein* a collar *is* disposed at a distal end of the implantable medical electrical lead, *and* wherein the [casing] *torque bearing member* is disposed within the collar, and *wherein the torque bearing member* is translatable along a longitudinal axis of the collar.

11. The [load-carrying body] *implantable medical electrical lead* of claim 10, [including] *wherein* a seal *is* disposed between the [casing] *torque bearing member* and the collar [for preventing], *the seal being configured to prevent* passage of ionic fluid into the lead through [its] *a* distal end *of the collar*.

12. The [load-carrying body] *implantable medical electrical lead* of claim 11, wherein the seal *disposed between the torque bearing member and the collar* is disposed at a distal end, [at] a proximal end, or along a middle of the [casing] *torque bearing member*.

13. The [load-carrying body] *implantable medical electrical lead* of claim [12] *6*, [including] *wherein* a collar *is* disposed at a distal end of the implantable medical electrical lead, *and* wherein the *distal* torque coupler is disposed within the collar, and *wherein the distal torque coupler* is translatable along a longitudinal axis of the collar.

14. The [load-carrying body] *implantable medical electrical lead* of claim 13, [including] *wherein* a seal *is* disposed between the *proximal* torque coupler and the collar [for preventing], *the seal being configured to prevent* passage of [bionic] *ionic* fluid into the lead through [its] *a* distal end *of the collar*.

15. The [load-carrying body] *implantable medical electrical lead* of claim 11, wherein the seal *disposed between the torque bearing member and the collar* is fixed relative to the [casing] *torque bearing member*.

16. The [load-carrying body] *implantable medical electrical lead* of claim 11, wherein the seal *disposed between the torque bearing member and the collar* is fixed relative to the collar.

17. The [load-carrying body] *implantable medical electrical lead* of claim 10, [including] *wherein* an insulative conformal coating *is* disposed about at least a portion of the [casing] *torque bearing member*.

18. The [load-carrying body] *implantable medical electrical lead* of claim 17, wherein the conformal coating comprises a dielectric ceramic coating.

19. The [load-carrying body] *implantable medical electrical lead* of claim 17, wherein the conformal coating is *characterized as having been* applied by *one of the group consisting of* sputtering, chemical vapor deposition, physical vapor deposition, dipping in [or] *a chemical solution and* applying a chemical solution.

20. The [load-carrying body] *implantable medical electrical lead* of claim 17, wherein the conformal coating comprises alumina or parylene.

21. The [load-carrying body] *implantable medical electrical lead* of claim [10] *1*, wherein the [casing] *torque bearing member* comprises a dielectric ceramic coating.

22. The [load-carrying body] *implantable medical electrical lead* of claim [10] *1*, wherein the [casing] *torque bearing member* comprises alumina.

23. The [load-carrying body] *implantable medical electrical lead* of claim 1, [including] *wherein* a unitary torque coupler *is* disposed over the [casing] *torque bearing member*.

* * * * *